US005700474A

United States Patent [19]
Preiser et al.

[11] Patent Number: 5,700,474
[45] Date of Patent: Dec. 23, 1997

[54] BIRD AVERSION COMPOSITIONS

[75] Inventors: Marvin F. Preiser, Middletown, N.Y.; Peter F. Vogt, Loveland, Ohio

[73] Assignee: PMC Specialties Group Inc., Rocky River, Ohio

[21] Appl. No.: 710,774

[22] Filed: Sep. 19, 1996

Related U.S. Application Data

[63] Continuation of Ser. No. 277,256, Jul. 20, 1994, abandoned, which is a continuation of Ser. No. 8,675, Jan. 25, 1993, abandoned.

[51] Int. Cl.$^6$ .................................................. A01N 25/02
[52] U.S. Cl. ........................................ 424/405; 514/918
[58] Field of Search ................................ 424/405; 512/1, 512/5, 20, 21, 22; 514/918

[56] References Cited

U.S. PATENT DOCUMENTS

| | | | |
|---|---|---|---|
| 2,967,128 | 1/1961 | Kare | 514/535 |
| 4,474,798 | 10/1984 | Inagi et al. | 514/420 |
| 4,626,274 | 12/1986 | Hausmann et al. | 504/229 |
| 4,663,315 | 5/1987 | Hasegawa et al. | 424/76.3 |
| 4,735,803 | 4/1988 | Katz et al. | 424/195.1 |
| 4,790,990 | 12/1988 | Mason et al. | 424/438 |
| 5,196,451 | 3/1993 | Greig-Smith et al. | 514/570 |
| 5,296,226 | 3/1994 | Askham | 424/405 |
| 5,364,626 | 11/1994 | Hasegawa et al. | 424/403 |

FOREIGN PATENT DOCUMENTS

| | | |
|---|---|---|
| 0173410-A1 | 3/1986 | European Pat. Off. . |
| 58-189115 | 11/1983 | Japan . |
| 1-110602 | 4/1989 | Japan . |

OTHER PUBLICATIONS

Dolbeer et al., "PEN Test of Methyl Anthranilate as a Bird Repellent in Water", Proc. East. Wildl. Damage Control Conf., vol. 5, issued 1992, pp. 112–116.

Avery, Michael, Proc. 15th Vertebrate Pest Conf., "Evaluation of Methyl Anthanilate as a Bird Repellent in Fruit Crops", pp. 130–133, (U.S.A., 1992).

Askham, Leonard, Proc. 15th Vertebrate Pest Conf., "Efficacy of Methyl Anthanilate as a Bird Repellent in Cherries, Blueberries and Grapes", pp. 137–141, (U.S.A., 1992).

Avery, Michael, et al., Chemical Signals in Vertebrates VI, "Use of a Trigeminal Irritant for Wildlife Management", pp. 319–322 (U.S.A., 1992).

Dolbeer, Richard et al., Proc. East Wildl. Damage Control Conf., "Pen Tests of Methyl Anthranilate as a Bird Repellent in Water", pp. 112–116, (U.S.A., 1992).

Dolbeer, Richard et al., 11th Great Plains Wildlife Damage Control Workshop Proceedings, "Methyl Athranilate Formulations to Repel Birds from Water at Airports and Food at Landfills", pp. 42–53, (U.S.A., Apr. 26–29, 1993).

Dolbeer, Richard and Clark, L., "Preliminary Field Evaluation of Methyl Anthranilate as a Bird Repellent in Temporary Pools of Water on Airports", Special Report–Not Published.

Belant, Jerrold "Methyl Anthranilate Formulations Repel Gulls and Mallards from Water", Special Report–Not Published.

Mason et al., Journal of Wildlife Management, "Anthranilate Repellency To Starlings: Chemical Correlates And Sensory Perception", vol. 53:(1), pp. 55–64 (U.S.A. 1989).

Mason et al., Journal of Wildlife Management, "Field Evaluation Of Dimethyl Anthranilate As A Bird Repellent Livestock Feed Additive", vol. 49:(3), pp. 636–642 (U.S.A. 1985).

Glahn et al., Wildlife Society Bulletin, "Dimethyl Anthranilate As A Bird Repellent In Livestock Feed", vol. 17, pp. 313–320 (U.S.A. 1989).

Crocker et al., IBIS, "Plant Chemistry And Bird Repellents", vol. 132 pp. 300–308 (U.K. 1990).

*Primary Examiner*—George F. Lesmes
*Assistant Examiner*—Robert H. Harrison
*Attorney, Agent, or Firm*—James M. Verna

[57] ABSTRACT

A liquid bird aversion solution having methyl anthranilate in an amount of from 15 to 50% by weight of a total weight of the solution; d-limonene in an amount of from 10 to 50% by weight of a total weight of the solution; and isopropyl myristate in an amount of from 10 to 50% by weight of a total weight of the solution. The liquid solution is lighter than water and forms a thin liquid film on a surface of a source when applied to the source.

12 Claims, No Drawings

BIRD AVERSION COMPOSITIONS

This is a continuation of application Ser. No. 08/277,256, filed Jul. 20, 1994 which was abandoned upon the filing hereof, which in turn is a continuation of application Ser. No. 08/008,675, filed Jan. 25, 1993 which was also abandoned.

BACKGROUND OF THE INVENTION

1. Field of the Invention

The present invention relates generally to new formulations of bird aversion compounds.

2. Prior Art

Methyl and dimethyl anthranilate (MA and DMA, respectively) are ester derivatives of anthranilic acid (also known as ortho-amino-benzoic acid). MA, DMA and other derivatives of anthranilic acid as well as esters of phenylacetic acid, are known to be bird aversion agents with preferred embodiments as feed additives to deter feed loss (U.S. Pat. No. 2,967,128 and 4,790,990), and as an anti-grazing compound for geese and swans (Mason, J. R. et al., "Anthranilate Repellency to Starlings: Chemical Correlates and Sensory Perception", JOURNAL OF WILDLIFE MANAGEMENT, 53:55–64 (1989)). Cinnamamide has also been shown to be a bird aversion agent. (Crocker & Perry, PLANT CHEMISTRY AND BIRD REPELLENTS, 132:300–308 (1990)).

U.S. Pat. No. 2,967,128 discloses the incorporation of MA and other ester derivatives of anthranilic acid as bird aversion agents into feed or pesticide additives, or into liquids to be sprayed on material. U.S. Pat. No. 4,790,990 teaches that the aversion agent can be at least partially trapped in a solid vehicle to improve its persistency. The solid vehicle can be a modified starch, oil or polymer which microencapsulates the aversion agent.

However, these prior art formulations have not proven entirely satisfactory, and there is still a continuing need to develop new formulations of bird aversion compounds.

In addition, prior art bird aversion formulations cannot be used for all conditions. For instance, these prior art bird repellents are heavier than water, e.g. methyl anthranilate has a density of 1.16. Thus, the prior art bird aversion compounds sink in water and as a consequence, they are not capable of repelling birds. Other mixtures of vegetable oils and bird aversion agents clump or coagulate in messy globs on the surface of water, which are not capable of repelling birds.

There is a need for bird aversion compounds which are capable of remaining at or near the surface of the water. This is especially true at airports located near bodies of water, where birds pose a potential danger or at fisheries, where birds eat the fish. Another area where a lighter than water bird aversion agent is required is at airports, where after rains or snows, puddles form on runways and other areas. These puddles attract birds which again pose a potential danger for the aircraft. Accordingly, there is a great need for bird aversion compounds which are lighter than water.

SUMMARY OF THE INVENTION

In one embodiment, the present invention is a formulation of a solid free flowing compound consisting essentially of a bird aversion agent in an amount of from 10 to 80%, preferably from 30 to 75%, by weight of a total weight of the compound; and an inorganic or organic carrier in an amount of from 20 to 90%, preferably from 25 to 70%, by weight of a total weight of the compound. Also, UV stabilizers, antioxidants and "lakes" or colors can be added in small concentrations, usually below 1% by weight of the total weight of the final product.

In another embodiment, the present invention concerns a bird aversion solution which is lighter than water. The liquid formulation comprises a bird aversion agent in an amount of from 5 to 50% by weight of a total weight of the solution; a terpene hydrocarbon and oxygenated derivative thereof in an amount of from 10 to 50% by weight of a total weight of the solution; and alkylesters selected from the group consisting of saturated fatty acids having from 4–20 carbon atoms and unsaturated fatty acids having from 10–18 carbon atoms esterified with an alcohol having from 1–8 carbon atoms in an amount of from 10 to 50% by weight of a total weight of the solution.

In another form, the bird aversion compound is an emulsion, consisting essentially of a bird aversion agent in an amount of from 5 to 30% by weight of a total weight of the emulsion; a terpene hydrocarbon and oxygenated derivative thereof in an amount of from 5 to 10% by weight of a total weight of the emulsion; gums selected from the group consisting of storage polysaccharides, pectins, gelatins, xanthans, cellulose derivatives and alginate in an amount of from 0.5 to 10% by weight of a total weight of the emulsion; and water in an amount of from 70 to 80% by weight of a total weight of the emulsion.

In all the embodiments of the present invention, the bird aversion agent is selected from the group consisting of methyl anthranilate, methyl phenyl acetate, ethyl phenyl acetate, ortho-amino acetophenone, 2-amino-4,5-dimethyl acetophenone, veratroyl amine, dimethyl anthranilate, cinnamic aldehyde, cinnamamide, cinnamic acid and combinations thereof.

DETAILED DESCRIPTION OF INVENTION

As used herein, the terms "bird(s)" refers to members of the class "Aves".

I. Solid Free Flowing Form

A formulation in a solid free flowing form, consists essential of from 10–80%, or preferably from 30–75%, by weight of the total weight of the solid form of a bird aversion agent; and 20–90%, preferably from 25–70%, by weight of the total weight of the solid form of a carrier. The bird aversion agent is selected from the group consisting of as methyl anthranilate, ortho-amino acetophenone, methyl phenyl acetate, ethyl phenyl acetate, veratroyl amine, 2-amino-4,5-dimethyl acetophenone, dimethyl anthranilate, cinnamamide, cinnamic acid, cinnamic aldehyde and combinations thereof. The carrier may be inorganic, organic or combinations of both. Examples of acceptable inorganic carriers are precipitated silica, such as silicon dioxide hydrate, e.g. SIPERNAT 22 HR from the North American Silica Company and talc. Examples of acceptable organic carriers are methacrylate ester copolymer, e.g. POLYTRAP Q5-6603 polymer powder from Dow Corning Corporation and calcium carbonate. When calcium carbonate and talc are used in the solid formulation either together or separately, they are added in amounts of from 40%–65% by weight of the total weight of the compound together with 1–10% silicon hydrate. Optionally, "lakes" or colors, ultra violet stabilizers and antioxidants can each be added in amounts of from 0 to 1% by weight of the total weight of the compound. In this amount, they do not affect the formulation. Examples of antioxidants are BHA, BHT and ethoxyquin, and some examples of colors are D&C violet #2 and FD&C blue #1.

By way of an example, the solid free flowing form may be prepared by first charging the "carrier" into a mixer or ribbon blender. The bird aversion agent, e.g. dimethyl anthranilate, is slowly added, via a metering pump, or by gravity feed, while the blender is in operation. Upon completion of the addition, samples are taken to verify complete homogenization of the active ingredient. The final product may be sifted through a 20–80 mesh screen to ensure uniform particle size. Optional "lakes" or colors may be added during the blending operation if so desired. The final product is analyzed for the bird aversion agent.

The following are only examples of some of the solid free flowing formulations:

| EXAMPLE Ia: | |
|---|---|
| Methyl and/or dimethyl anthranilate | 35–60% |
| Silicon dioxide hydrate | 65–40% |
| D&C Violet #2 and/or FD&C Blue #1 | 0–1% |
| EXAMPLE Ib: | |
| Ortho-amino acetophenone | 35–60% |
| Silicon dioxide hydrate | 65–40% |
| EXAMPLE Ic: | |
| Cinnamamide | 40–60% |
| Silicon dioxide hydrate | 60–40% |
| D&C Violet #2 and/or FD&C Blue #1 | 0–1% |
| EXAMPLE Id: | |
| Methyl phenyl acetate | 40–60% |
| Silicon dioxide hydrate | 60–40% |
| EXAMPLE Ie: | |
| Methyl or dimethyl anthranilate | 50% |
| Silicon dioxide hydrate | 50% |
| EXAMPLE If: | |
| Methyl anthranilate | 60–80% |
| Methacrylate ester copolymer | 40–20% |
| EXAMPLE Ig: | |
| Dimethyl anthranilate | 60–80% |
| Methacrylate ester copolymer | 40–20% |
| EXAMPLE Ih: | |
| Ortho-amino acetophenone | 55–75% |
| Methacrylate ester copolymer | 45–25% |
| EXAMPLE Ii: | |
| Cinnamic aldehyde | 50–80% |
| Methacrylate ester copolymer | 50–20% |
| EXAMPLE Ij: | |
| Dimethyl anthranilate | 75% |
| Methacrylate ester copolymer | 25% |
| EXAMPLE Ik: | |
| Methyl and/or dimethyl anthranilate | 10–30% |
| Methacrylate ester copolymer | 25–10% |
| Clay | 65–60% |
| EXAMPLE Il: | |
| Cinnamic acid or aldehyde | 10–30% |
| Methacrylate ester copolymer | 25–10% |
| Clay | 65–60% |
| EXAMPLE Im: | |
| Veratroyl amine | 10–30% |
| Methacrylate ester copolymer | 25–10% |
| Clay | 65–60% |
| EXAMPLE In: | |
| Methyl anthranilate | 25% |
| Methacrylate ester copolymer | 10% |
| Clay | 65% |

| -continued | |
|---|---|
| EXAMPLE Io: | |
| Methyl and/or dimethyl anthranilate | 35–55% |
| Calcium carbonate and/or talc | 65–40% |
| Silicon dioxide hydrate | 10–1% |
| EXAMPLE Ip: | |
| Cinnamic acid or aldehyde | 15–45% |
| Calcium carbonate and/or talc | 65–40% |
| Silicon dioxide hydrate | 10–1% |

II. Liquid Form (Lighter Than Water)

In another embodiment the present invention relates to a liquid formulation that is lighter than water and forms a thin liquid film on the water surface. The present invention formulation is made lighter than water by dissolving the bird aversion agent in a mixture of terpene hydrocarbons and oxygenated derivatives together with aliphatic mono-esters.

The bird aversion agent is selected from the group consisting of as methyl anthranilate, methyl phenyl acetate, ethyl phenyl acetate, ortho-amino acetophenone, 2-amino-4,5-dimethyl acetophenone, veratroyl amine, dimethyl anthranilate, cinnamic aldehyde, cinnamamide, cinnamic acid and combinations thereof. The bird aversion agent used in this formulation is in an amount of from 5 to 50%, preferably from 10 to 40%, and more preferably from 30 to 40% by weight of the total weight of the solution.

The terpene hydrocarbon and oxygenated derivatives comprise from 10 to 50%, preferably 20–40%, and more preferably 25–35% by weight of a total weight of the solution. The terpene hydrocarbon and oxygenated derivatives are selected from limonene, di-pentene, alpha-pinene, beta-pinene, caryophyllene, and p-cymene. The preferred terpene hydrocarbon and oxygenated derivative is d-limonene. A terpene hydrocarbon and oxygenated derivative is used because it is inert and reduces specific gravity.

The alkylesters which comprise from 10 to 50% by weight of a total weight of the solution are selected from saturated fatty acids having from 4 to 20 carbon atoms, unsaturated fatty acids having from 10 to 18 carbon atoms, including oleic, ricinoleic and linoleic acid esterified with an alcohol having from 1 to 8 carbon atoms, such as methyl to octyl alcohol, preferably isopropyl alcohol. Examples of some of the alkylesters are iso-propyl myristate, liquid petrolatum, castor oil, glyceryl trioleate and glyceryl palmitate.

Optionally, solubilizers, such as ethoxy alkalated phenols, may be added in amounts of from 10–40% by weight of the total weight of the solution. Examples of ethoxy alkalated are octoxynols, such as octyl phenoxy polyethoxyethanol (octoxynol 9 or TRITON X-100), and nonoxynols, such as nonoxynol 10. Also, a coloring dye may be added in an amount of from 0 to 1% by weight of the total weight of the solution. An exemplary color is D&C violet #2. An antioxidant, such as BHT, BHA and ethoxyquin may also be added in an amount of from 0 to 0.5% by weight of the total weight of the solution.

The following are only examples of some of the liquid formulations:

| EXAMPLE IIa: | |
|---|---|
| Methyl anthranilate | 35–50% |
| D-limonene | 25–35% |
| Iso-propyl myristate | 25–40% |
| D&C Violet #2 | 0–1% |

-continued

| EXAMPLE IIb: | |
|---|---|
| Dimethyl anthranilate | 30-45% |
| D-limonene | 20-40% |
| Iso-propyl myristate | 10-30% |
| EXAMPLE IIc: | |
| Methyl anthranilate | 4.0% |
| D-limonene | 30% |
| Iso-propyl myristate | 30% |
| EXAMPLE IId: | |
| Dimethyl anthranilate | 35-45% |
| Caryophyllene | 20-40% |
| Iso-propyl myristate | 30-50% |
| EXAMPLE IIe: | |
| Methyl phenyl acetate and/or Ethyl phenyl acetate | 20-40% |
| D-limonene | 30% |
| Iso-propyl myristate | 20-35% |
| D&C Violet #2 | 0-1% |
| EXAMPLE IIf: | |
| Ortho-amino acetophenone | 20-40% |
| Di-pentene | 25-30% |
| Octyl phenoxy polyethoxyethanol | 10-40% |
| EXAMPLE IIg: | |
| Cinnamamide | 20-40% |
| Di-pentene | 25-30% |
| Iso-propyl myristate | 25-40% |
| D&C Violet #2 | 0-1% |
| EXAMPLE IIh: | |
| 2-amino-4,5-dimethyl acetophenone | 25-35% |
| Alpha and/or beta-pinenes | 10-30% |
| Nonoxynol 10 | 20-35% |
| EXAMPLE IIi: | |
| Methyl anthranilate and Dimethyl anthranilate | 5-50% |
| D-Limonene | 25-50% |
| Iso-propyl myristate | 10-30% |
| EXAMPLE IIj: | |
| Veratroyl amide | 5-15% |
| Methyl phenyl acetate and Ethyl phenyl acetate | 5-15% |
| Di-pentene | 20-35% |
| Castor Oil | 15-25% |
| EXAMPLE IIk: | |
| 2-amino-4,5-dimethyl acetophenone | 20-40% |
| Caryophyllene | 10-30% |
| Glyceryl Trioleate/Tripalmitate | 20-35% |
| EXAMPLE II: | |
| Cinnamic aldehyde or cinnamic acid | 15-45% |
| P-cymene | 25-50% |
| Iso-propyl myristate | 25-35% |
| EXAMPLE IIm: | |
| Cinnamic aldehyde or cinnamic acid | 10-40% |
| Alpha and/or beta-pinenes | 15-45% |
| Glyceryl Trioleate/Tripalmitate | 20-35% |

By way example only, a liquid "lighter than water" formulation was prepared by adding to a clean container, 80 g methyl anthranilate, 60 g iso-propyl myristate, and 60 g d-limonene. Additional ingredients such as antioxidants may also be added.

All materials except color are added sequentially under continuous agitation. If color is to be added, it is added after completely blending of the other ingredients. The finished product may be filtered prior to packaging. The final product is analyzed for methyl anthranilate.

III. Emulsion Water-dispersible

In a still further embodiment, the present invention relates to an emulsion formulation miscible with water, containing terpene hydrocarbons and gums to form a polymeric film on plant leaves and fruits. The formulation consists essentially of a bird aversion agent in an amount of from 5 to 30%, preferably from 10 to 20%, and more preferably 12% by weight of the total weight of the emulsion, a terpene hydrocarbon from 5 to 10% by weight of the total weight of the emulsion, and gum from 0.5 to 10%, preferably from 3 to 4% by weight of the total weight of the emulsion, with the remaining portion of the emulsion being water. Optionally, citric acid, sodium benzoate, colors may each be added in amounts of from 0 to 1% by weight of the total weight of the emulsion for stabilization and for appearance.

The bird aversion agent is selected from the group consisting of as methyl anthranilate, methyl phenyl acetate, ethyl phenyl acetate, ortho-amino acetophenone, 2-amino-4,5-dimethyl acetophenone, veratroyl amine, dimethyl anthranilate, cinnamic aldehyde, cinnamamide, cinnamic acid and combinations thereof.

The gums are selected from polysaccharides, such as arabic, karaya, guar, tragacanth or pectin (carbohydrates), gelatins (proteins), xanthans, cellulose derivative or alginate (carbohydrates) and combinations thereof. Some exemplary gums are KETROL (a xanthan), EMUL (a gum arabic), KELGIN F and KELCO-GEL (alginates), locust bean gum and malto-dextrins.

The terpene is selected from limonene, di-pentene, alpha-pinene, beta-pinene, caryophyllene, p-cymene and combinations thereof. The preferred terpene is d-limonene. In this formulation, the terpene is used as an organic solvent.

The following are only examples of some of the emulsion formulations:

| EXAMPLE IIIa: | |
|---|---|
| Methyl and/or dimethyl anthranilate | 10-15% |
| d-Limonene | 5-10% |
| Xanthan gum (KELTROL) | 0.5-5% |
| Gum arabic (EMUL) | 1-5% |
| FD&C Blue #1 | 0-1% |
| Water | 70-80% |
| EXAMPLE IIIb: | |
| Methyl and/or dimethyl anthranilate | 10-20% |
| Di-pentene | 5-10% |
| Gum karaya | 0.5 . 5% |
| Gum arabic (EMUL) | 1-5% |
| Water | 70-80% |
| EXAMPLE IIIc: | |
| Cinnamamide | 5-15% |
| Di-pentene | 5-10% |
| Xanthan gum | 0.5 . 5% |
| Gum arabic | 1-5% |
| FD&C Blue #1 | 0-1% |
| Water | 70-85% |
| EXAMPLE IIId: | |
| Methyl anthranilate | 13% |
| d-Limonene | 9% |
| Xanthan gum | 0.5% |
| Gum arabic | 3% |
| Water | 75% |
| EXAMPLE IIIe: | |
| Ortho-amino acetophenone | 5-30% |
| Alpha and/or beta pintenes | 5-10% |
| Xanthan gum (KELTROL) | 0.5 . 5% |
| Locust bean gum | 1-5% |
| FD&C Blue #1 | 0-1% |
| Water | 55-85% |

-continued

EXAMPLE IIIf:

| | |
|---|---|
| Ethyl and/or methyl phenyl acetate | 10–15% |
| d-Limonene | 5–10% |
| Gum tragacanth | 0.5 . 5% |
| Malto-dextrins | 1–5% |
| Water | 55–80% |

EXAMPLE IIIg:

| | |
|---|---|
| 2-amino-4,5-dimethyl acetophenone | 10–25% |
| alpha and/or beta-pinene | 5–10% |
| Alginate gum (KELCO-GEL) | 0.5 . 5% |
| Gum arabic (EMUL) | 1–5% |
| Water | 60–80% |

EXAMPLE IIIh:

| | |
|---|---|
| Veratroyl amine | 10–15% |
| Ethyl and/or methyl phenyl acetate | 10–15% |
| Di-pentene | 5–10% |
| Xanthan gum | 0.5–5% |
| Gum arabic | 1–5% |
| Water | 55–80% |

EXAMPLE IIIi:

| | |
|---|---|
| Methyl and/or dimethyl anthranilate | 5–30% |
| p-cymene | 5–10% |
| Alginate gum (KELGIN F) | 0.5 . 5% |
| Gum arabic (EMUL) | 1–5% |
| Water | 55–85% |

EXAMPLE IIIj:

| | |
|---|---|
| Cinnamic acid or aldehyde | 5–30% |
| Alpha and/or beta pintenes | 5–10% |
| Xanthan gum (KELTROL) | 0.5 . 5% |
| Locust bean gum | 1–5% |
| Water | 65–80% |

EXAMPLE IIIk:

| | |
|---|---|
| Methyl and/or dimethyl anthranilate | 5–30% |
| Caryophylene | 5–10% |
| Xanthan gum | 0.5 . 5% |
| Gum arabic | 1–5% |
| Water | 55–85% |

By way of example only, an emulsion was prepared by mixing the "gums", e.g. 6 g of gum arabic (such as EMUL BV IRX 2900), with 150.2 g of water, and heating to about 50° C. Using a homogenizer, the "gums" are dispersed in water free of lumps. At this point 1.0 g of another gum such as a xanthan (for example KELTROL polysaccharide gum) is added under continued agitation until homogenized. When complete suspension, free of lumps, is obtained, a premix consisting of a blend of 16.8 g of a terpene, for example caryophyllene, and 25.4 g of a bird aversion agent, such as cinnamamide, is slowly added under continued agitation until a stable emulsion is obtained. Additional ingredients such as 0.2 g citric acid and 0.4 g sodium benzoate may be added for stability. The final product is analyzed for the content of bird aversion agent.

The foregoing description of the invention has been made with references with a few preferred embodiments. Persons skilled in the art will understand that changes and modifications can be made in the invention without departing from the spirit and scope of the claims as follows.

We claim:

1. A liquid bird aversion solution, comprising:

methyl anthranilate in an amount of from 15 to 50% by weight of the total weight of the solution;

d-limonene in an amount of from 10 to 50% by weight of the total weight of the solution; and isopropyl myristate in an amount of from 10 to 50% by weight of the total weight of the solution, wherein the liquid solution is lighter than water and forms a thin liquid film on a surface when applied to a source.

2. The solution of claim 1, further comprising:

a coloring dye in an amount of from 0 to 1% by weight of the total weight of the solution.

3. The solution of claim 1, wherein the methyl anthranilate is from 15 to 40% by weight of the total weight of the solution.

4. The solution of claim 1, wherein the methyl anthranilate is from 30 to 40% by weight of the total weight of the solution.

5. The solution of claim 1, wherein the d-limonene is from 20 to 40% by weight of the total weight of the solution.

6. The solution of claim 1, wherein the d-limonene is from 25 to 35% by weight of the total weight of the solution.

7. A liquid bird aversion solution for application to a water source, comprising:

methyl anthranilate in an amount of from 15 to 50% by weight of the total weight of the solution;

d-limonene in an amount of from 10 to 50% by weight of the total weight of the solution; and isopropyl myristate in an amount of from 10 to 50% by weight of the total weight of the solution, wherein the liquid solution is lighter than water and forms a thin liquid film on a surface of said water source when applied to said water source.

8. The solution of claim 7, further comprising:

a coloring dye in an amount of from 0 to 1% by weight of the total weight of the solution.

9. The solution of claim 7, wherein the methyl anthranilate is from 15 to 40% by weight of the total weight of the solution.

10. The solution of claim 7, wherein the methyl anthranilate is from 30 to 40% by weight of the total weight of the solution.

11. The solution of claim 7, wherein the d-limonene is from 20 to 40% by weight of the total weight of the solution.

12. The solution of claim 7, wherein the d-limonene is from 25 to 35% by weight of the total weight of the solution.

* * * * *